US011324475B2

(12) United States Patent
Conwell (10) Patent No.: US 11,324,475 B2
(45) Date of Patent: May 10, 2022

(54) HANDHELD SURGICAL DEVICES WITH TACTILE OPERABLE CONTROLS

(71) Applicant: Faxitron Bioptics, LLC, Marlborough, MA (US)

(72) Inventor: Richard L. Conwell, San Diego, CA (US)

(73) Assignee: Faxitron Bioptics, LLC, Marlborough, MA (US)

( * ) Notice: Subject to any disclaimer, the term of this patent is extended or adjusted under 35 U.S.C. 154(b) by 706 days.

(21) Appl. No.: 15/990,527

(22) Filed: May 25, 2018

(65) Prior Publication Data
US 2019/0357871 A1 Nov. 28, 2019

(51) Int. Cl.
*A61B 6/00* (2006.01)
*A61B 1/06* (2006.01)
*A61B 90/00* (2016.01)

(52) U.S. Cl.
CPC ............ *A61B 6/547* (2013.01); *A61B 1/06* (2013.01); *A61B 6/4057* (2013.01);
(Continued)

(58) Field of Classification Search
CPC ......... A61B 6/547; A61B 6/4057; A61B 1/06; A61B 90/39; A61B 6/4423; A61B 2090/397; A61B 6/425; A61B 6/4258; A61B 6/566; A61B 2090/0811; A61B 2090/306; A61B 2090/309; A61B 2090/392
See application file for complete search history.

(56) References Cited

U.S. PATENT DOCUMENTS 5,036,201 A 7/1991 Carroll et al.
5,573,493 A * 11/1996 Sauer ................. A61B 1/00101
600/121
(Continued)

FOREIGN PATENT DOCUMENTS

EP 2291679 3/2011
WO 2009/074959 6/2009

OTHER PUBLICATIONS

PCT International Search Report and Written Opinion in International Application PCT/US2018/034764, dated Aug. 24, 2018, 13 pgs.
(Continued)

*Primary Examiner* — Joel Lamprecht
(74) *Attorney, Agent, or Firm* — Merchant & Gould P.C.

(57) ABSTRACT

Disclosed are devices, systems and methods for providing sterile and cost-affordable handheld surgical devices with tactile operable controls. In some aspects, a surgical device includes a surgical probe including a probe detector and a set of operable controls; an exterior shell casing including an opening at one end leading to an interior cavity structured to have a size and shape to fit the surgical probe within and position the probe detector in a first region and a handle of the surgical probe in a second region, in which the first region of the exterior shell casing is configured to be inserted into an incision of a patient's body and the second region is configured to provide a user of the surgical device utilization of the operable controls of the surgical probe through the exterior shell casing; and a cap attachable to the exterior shell casing to close the opening.

21 Claims, 6 Drawing Sheets

(52) U.S. Cl.
CPC ............ *A61B 6/4423* (2013.01); *A61B 90/39* (2016.02); *A61B 2090/397* (2016.02)

(56) References Cited

U.S. PATENT DOCUMENTS

| | | |
|---|---|---|
| 5,732,704 A | 3/1998 | Thurston |
| 5,846,513 A | 12/1998 | Carroll et al. |
| 5,857,463 A | 1/1999 | Thurston et al. |
| 5,961,458 A | 10/1999 | Carroll |
| 6,191,422 B1 | 2/2001 | Thurston |
| 6,236,880 B1 | 5/2001 | Raylman et al. |
| 6,263,232 B1 | 7/2001 | Norman, Jr. |
| 6,331,703 B1 | 12/2001 | Yarnall et al. |
| 6,771,802 B1 | 8/2004 | Patt |
| 6,940,071 B2 | 9/2005 | Ramsden et al. |
| 7,202,478 B2 | 4/2007 | Ramsden et al. |
| 8,816,292 B2 | 8/2014 | Cui et al. |
| 9,069,092 B2 | 6/2015 | Oreper |
| 9,155,529 B2 | 10/2015 | Beardsley |
| 9,498,108 B1 | 11/2016 | Lombardi |
| 10,310,097 B2 | 6/2019 | Yarnall |
| 11,199,632 B2 | 12/2021 | Yarnall |
| 2003/0183768 A1 | 10/2003 | Miller et al. |
| 2004/0054248 A1 | 3/2004 | Kimchy et al. |
| 2005/0263711 A1 | 12/2005 | Gerl et al. |
| 2008/0058637 A1 | 3/2008 | Fischell |
| 2008/0080593 A1* | 4/2008 | Lane ............... G01K 13/20 374/208 |
| 2011/0071362 A1* | 3/2011 | Reicher ............. A61B 17/0218 600/217 |
| 2013/0116771 A1* | 5/2013 | Robinson ............... A61F 2/966 623/1.11 |
| 2013/0150729 A1* | 6/2013 | Zuluage ............. A61B 5/0088 600/476 |
| 2014/0249402 A1 | 9/2014 | Kimchy |
| 2016/0170035 A1* | 6/2016 | Yarnall ................... G01T 1/161 600/436 |
| 2018/0055596 A1* | 3/2018 | Johnson ................ A61B 90/30 |

OTHER PUBLICATIONS

PCT Preliminary Search Report on Patentability in International Application PCT/US2018/034764, dated Oct. 10, 2019, 8 pgs.

* cited by examiner

Surgical Apparatus 120 (e.g., non-sterile probe core) partially inserted into sterile Exterior Casing Unit 110

FIG. 4

Surgical Apparatus 120 (e.g., non-sterile probe core) fully inserted into sterile Exterior Casing Unit 110, with cap 130 positioned for sealing

FIG. 5

Surgical Apparatus 120 (e.g., non-sterile probe core) fully inserted into sterile Exterior Casing Unit 110 and sealed by Cap 130, with operable controls of surgical apparatus 120 accessible and ready-for-use

HANDHELD SURGICAL DEVICES WITH TACTILE OPERABLE CONTROLS

CROSS-REFERENCE TO RELATED APPLICATIONS

U.S. Provisional Patent Application No. 62/477,097, entitled "STERILE EXOSHELL WITH OPERABLE CONTROLS FOR SURGICAL PROBE" filed on Mar. 27, 2017. The entire content of the aforementioned patent application is incorporated by reference as part of the disclosure of this patent document.

TECHNICAL FIELD

This patent document relates to surgical instruments.

BACKGROUND

In medicine, handheld nuclear-uptake probes are often used to locate structures and regions where injected radionuclides are present. For example, a handheld nuclear probe device can be used in radio-guided parathyroid and sentinel lymph node surgery with injected Tc-99 sestamibi and Tc-99 sulfur colloid radiotracers. Some probes have parameters that may be changed during use. To reduce confusion and time, it is best if the controls for affecting these changes are positioned on the probe, thereby allowing the surgeon to be in control.

SUMMARY

Disclosed are devices, systems and methods for providing sterile and cost effective handheld surgical devices with tactile operable controls.

In some aspects, a surgical device includes a surgical probe including a probe detector, a data processing unit, and a set of operable controls; an exterior shell casing including an opening at one end leading to an interior cavity structured to have a size and shape to fit the surgical probe within and position the probe detector in a first region and a handle of the surgical probe in a second region, in which the first region of the exterior shell casing is configured to be inserted into an incision of a patient's body and the second region is configured to provide a user of the surgical device access to the set of operable controls of the surgical probe; and an end cap attachable to the exterior shell casing to close the opening.

In some aspects, a sterile exoshell for a handheld surgical apparatus includes an exterior shell casing including a first region and a second region, the exterior shell casing structured to include an opening at one end in the second region and an interior cavity of a size and shape to fit a surgical apparatus within the exterior shell casing that positions a first component in the first region and positions a set of operable controls that affect one or more parameters of the first component in the second region, the exterior shell casing including a control interface structure located in the second region to allow utilization of the set of operable controls through the exterior shell casing, the first region of the exterior shell casing is configured to be inserted into an incision of a body and the second region is configured to provide access to the set of operable controls of the surgical probe; and an end cap attachable to the exterior shell casing to close the opening.

In some aspects, a surgical device includes a surgical probe, including a probe detector located in a distal region of the surgical probe, a set of operable controls located in a proximal region of the surgical probe to allow a user to affect one or more parameters of the probe detector, and a data processing unit to process data associated with the probe detector and the set of operable controls; an exterior shell casing including a first region and a second region, the exterior shell casing structured to include an opening at one end in the second region and an interior cavity of a size and shape to fit the surgical probe within the exterior shell casing that positions the probe detector in the first region and positions the set of operable controls in the second region, which the first region of the exterior shell casing is configured to be inserted into an incision of a body and the second region is configured to provide access to the set of operable controls of the surgical probe; and an end cap attachable to the exterior shell casing to close the opening.

Implementations of the disclosed devices, systems and methods can include one or more of the following features. In some implementations, the disclosed technology include sterile and disposable exterior structures for surgical devices that provide direct sensory contacts of operable controls of the encased surgical device, such as a non-sterile, low-cost, durable surgical probe device. In some implementations, a sterile and disposable exterior structure encases a low-cost, non-sterile, durable surgical probe core in an aseptic manner within the interior of the exterior structure (e.g., exoshell) through an opening at one end of the exoshell, in which the opening is then closed with a sterile cap.

The subject matter described in this patent document can be implemented in specific ways that provide one or more of the following features.

DETAILED DESCRIPTION

In medicine, hand-held nuclear uptake probes are used to detect concentrations of injected radionuclides, e.g., such as Tc-99m sestamibi and Tc-99m sulfur colloid. These probes typically include data processing and output means and are commonly used to guide parathyroid and sentinel lymph node surgeries using their audible signal and count-rate readout to locate structures and regions where injected radionuclides are present. Some probes have parameters that may be changed during use. To reduce confusion and time, it is best if the controls for affecting these changes are positioned on the probe, thereby allowing the surgeon to be in control.

Current durable surgical probes are made sterile for surgical use by either directly sterilizing the probe (e.g., low temperature steam sterilization prior to surgery) or by draping the probe with a pliable, sterile sheath. As direct, repeated sterilization of the durable probe may lead to gradual damage of the probe, the use of sterile sheaths is more common. Disposable surgical probe systems are typically sold sterile and do not require a sheath for sterility, but are expensive on a per-procedure cost basis due to their one-time use. Thus, non-sterile, durable surgical probe systems are more commonly used than sterile disposable surgical probe systems as they are typically financially advantageous, i.e., comparatively less expensive on a per-procedure basis, despite their susceptibility to damage from sterilization procedures and additional problems.

For example, existing low cost, non-sterile, durable surgical probe systems that are equipped with operable controls cause another level of complexity for a surgeon when using a sterile sheath to cover the device. The overlying sterile sheath makes it difficult for the surgeon to confidently use these controls since the sheath reduces sensory perception of the location of the controls. In addition, the presence of operable controls on a non-sterile, durable probe system exacerbates the problem of damage due to repeated, direct sterilization. Furthermore, the use of existing sheaths does not ensure sterility, as these sheaths often have perforations, e.g., either directly from incorrect manufacturing and/or packaging, or as a result of being perforated by other surgical used tools during the surgery.

Disclosed are devices, systems and methods for providing sterile and cost effective handheld surgical devices with tactile operable controls.

While the disclosed embodiments described herein are primarily related to handheld nuclear uptake probes for radionucleotide monitoring applications, it is understood that the disclosed embodiments can also include other medical devices with controls on the device used in other medical applications.

In some aspects, the disclosed devices include sterile and disposable exterior structures for encasing surgical devices, such as a non-sterile, low-cost, durable surgical probe device, which provide direct sensory contact with the surgical device's operable controls. In some embodiments, a sterile and disposable exterior structure, also referred to as an "exoshell", is engineered to provide a protective, sterile outer casing for a low-cost, non-sterile, durable surgical device (such as the handheld surgical probe core) in an aseptic manner within the interior of the exoshell through an opening at one end of the exoshell, in which the opening is then closed with a sterile cap.

Figure 1A:
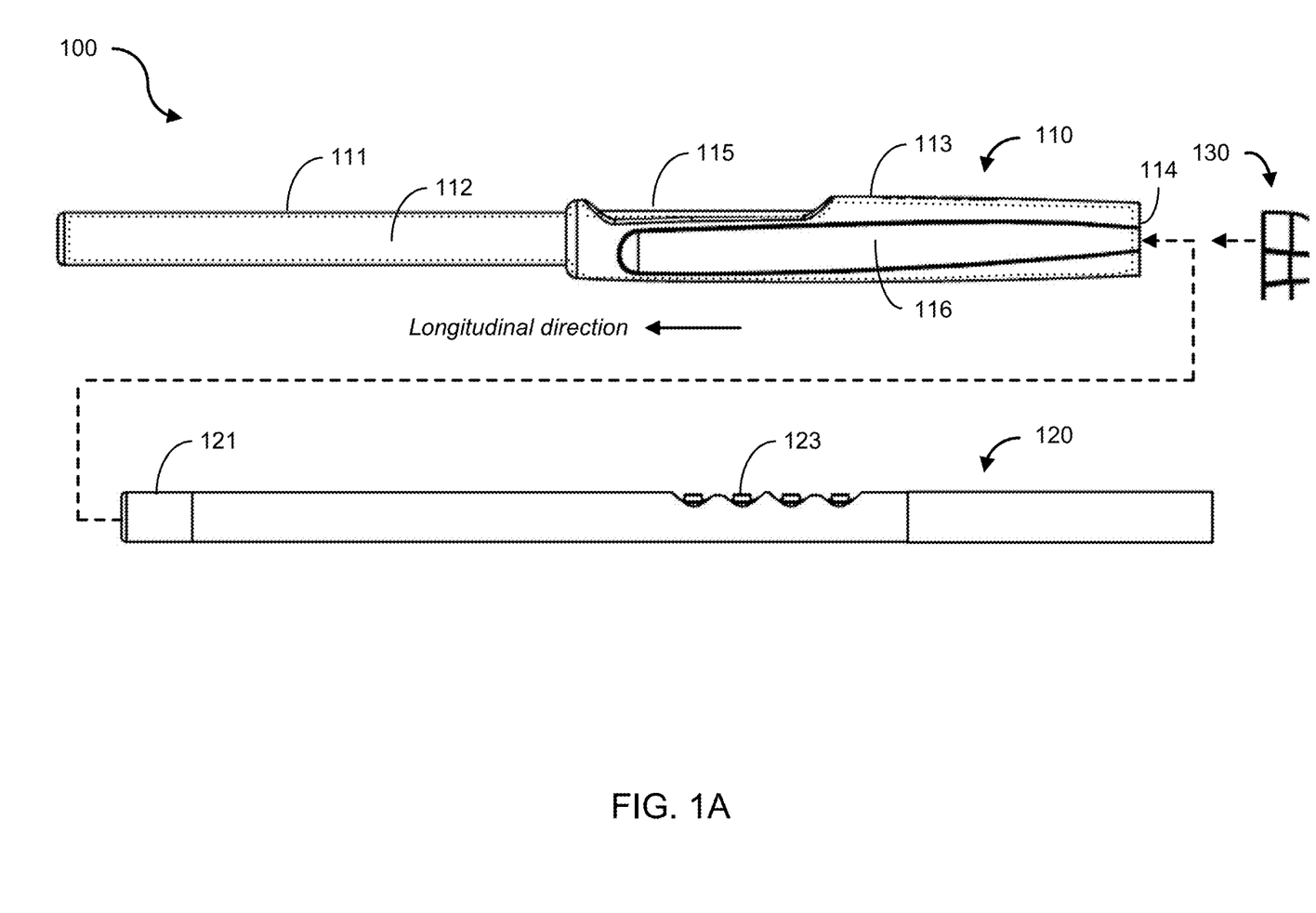
FIGS. 1A-1C show illustrative diagrams of example embodiments of a surgical device in accordance with the present technology.

FIG. 1A shows an illustrative diagram of an example embodiment of a surgical device 100 in accordance with the present technology which includes an exterior shell casing 110 and end cap 130 able to encase a surgical apparatus 120 having operable controls, forming a sterile, disposable exoshell to create sterility for the surgical apparatus 120 and provide a user the ability to utilize the operable controls through the sterile exoshell. In this example, the surgical apparatus 120 includes a surgical probe. The surgical probe includes a probe detector 121 located in a distal region of the surgical probe, e.g., such as a collimator and radiation sensor disposed at the distal end of the surgical probe. The surgical probe includes a set of operable controls 123 located in a proximal region of the surgical probe, which provide a physical structure for the user (e.g., surgeon) to interface in order to implement a corresponding set of one or more device controls that affect one or more parameters of operation of the surgical probe, such as affecting the operation of the probe detector 121, a device indicator, or other feature during surgical use. In some embodiments, the one or more operable controls of the surgical apparatus 120, such as the example surgical probe, can be embodied by a mechanical switch, a capacitive contact, a Hall sensor, a touch display, or other mechanism that affects the associated parameter with the corresponding control. For example, in some implementations, the set of operable controls 123 are arranged on the exterior of the surgical probe and receives contact when the user interfaces the operable controls through the exoshell; whereas, in some implementations, the set of operable controls 123 can include a sensor in the interior of the surgical probe that receives a signal when the user interfaces the sensor through the exoshell. The surgical probe includes a data processing unit 125 configured to process data associated with the probe detector 121 and the set of operable controls 123. In some embodiments, the data processing unit is incorporated within the surgical apparatus 120; whereas in some embodiments, the data processing unit can be incorporated in an external device in data communication with an electronics unit in the surgical apparatus 120. Other examples of surgical probes are described in U.S. Patent Publication No. 2016/0170035A1, entitled "GAMMA PROBE WITH HAND-PIECE CONTROL OF DETECTION PARAMETERS", which is incorporated by reference as part of this disclosure for all purposes.

The exterior shell casing 110 includes a first region 111 and a second region 113, in which there is an opening 114 in the second region 113. The exterior shell casing 110 includes a control interface structure located in the second region 113, e.g., embodied in the example of FIG. 1A as a flexible membrane 115. The exterior shell casing 110 includes an interior cavity 112 of a size and shape to allow the surgical apparatus 120 to fit within the exterior shell casing 110 in a manner that aligns the operable controls of the surgical apparatus 120 with the membrane 115. The flexible membrane 115 aligns with the set of operable controls of the surgical apparatus 120 to allow for actuation of the apparatus' controls by tactile interaction of a user's hand with the set of operable controls 123 through the flexible membrane 115. In the example shown in FIG. 1A, the interior cavity 112 of the exterior shell casing 110 is able to receive the example surgical probe apparatus 120, such that the probe detector 121 is positioned in the first region 111 of the exterior shell casing 110 and the set of operable controls 123 is positioned in the second region 113 of the exterior shell casing 110. For example, in implementations of the surgical device 100, the first region 111 is configured to be inserted into an incision of a body, and the second region 113 is configured to provide access to the set of operable controls of the surgical apparatus 120.

The end cap 130 is attachable a portion of the exterior shell casing 110 to close the opening 114 and thereby seal the surgical apparatus 120 in the exterior shell casing 110. The exterior shell casing 110 and the end cap 130 are sterile on at least their outer surfaces and are able to preserve sterility of the surgical device 100, i.e., the surgical apparatus 120 encased within, including when the surgical apparatus 120 is non-sterile. As such, the exterior shell casing 110 and the end cap 130 together form a sterile, disposable surgical accessory device that (i) protects the encased surgical apparatus 120 (e.g., probe device) while providing full, unimpeded access to its operating components, i.e., the controls, and use of its detector, (ii) effectively renders the encased surgical apparatus 120 as a sterile device through the protection of the exoshell, and (iii) allows for multiple reuse of lower-cost surgical apparatuses, thereby lowering the costs associated with health care procedures using these surgical devices.

In some embodiments, for example, the sterile exterior shell casing 110 includes a biocompatible material, e.g., to minimize or prevent adverse reaction of the sterile exterior shell casing 110 with biological tissue or substances when inserted inside a patient. In some examples, the sterile exterior shell casing 110 can include polycarbonate or polysulfone as the rigid material of the body of the exterior shell casing 110, and silicone rubber or polyurethane or other thermoplastic elastomeric material as the flexible membrane 115. Notably, the material of the sterile exterior shell casing 110 and the end cap 130 are compatible with a sterilization process, which may include gamma radiation, ethylene gas treatment, low temperature steam sterilization or autoclaving.

The interior cavity 112 of the exterior shell casing 110 can be structured to have a shape and size prefixed to substantially (e.g., closely) match the exterior shape and size of the surgical probe 120. The body of the exterior shell casing 110 can be configured with a flexible and/or stretchable material to allow tolerance between the exact sizes of the exterior shell casing 110 and the surgical apparatus 120. For example, a flexible and stretchable material of the exterior shell casing 110 can allow for protruding structures of the surgical probe to fit through the opening 114 that may be of a smaller size than the largest dimension of the surgical probe 120, and still provide a snug fit. As such, the interior cavity 112 of the exterior shell casing 110 can be structured to have a shape and size general to many different types of surgical apparatuses 120, and therefore still allow a larger surgical apparatus 120 to fit within the exterior shell casing 110 that interfaces the set of operable controls 123 with the flexible membrane 115.

In some embodiments, the exterior shell casing 110 can optionally include one or more external structural features 116 that may aid in gripping of the surgical device 100. In some examples, the one or more external structural features 116 includes a handle portion arranged on the exterior shell casing 110 to surround the location of the set of operable controls of the surgical apparatus 120. The example handle portion of the exterior shell casing 110 can include pliable silicon rubber.

In some embodiments, the exterior shell casing 110 can include structures located within a region at least partially occupied by the flexible membrane 115 to further enhance the ability of the user to actuate the set of operable controls of the surgical apparatus 120.

Figure 1B:
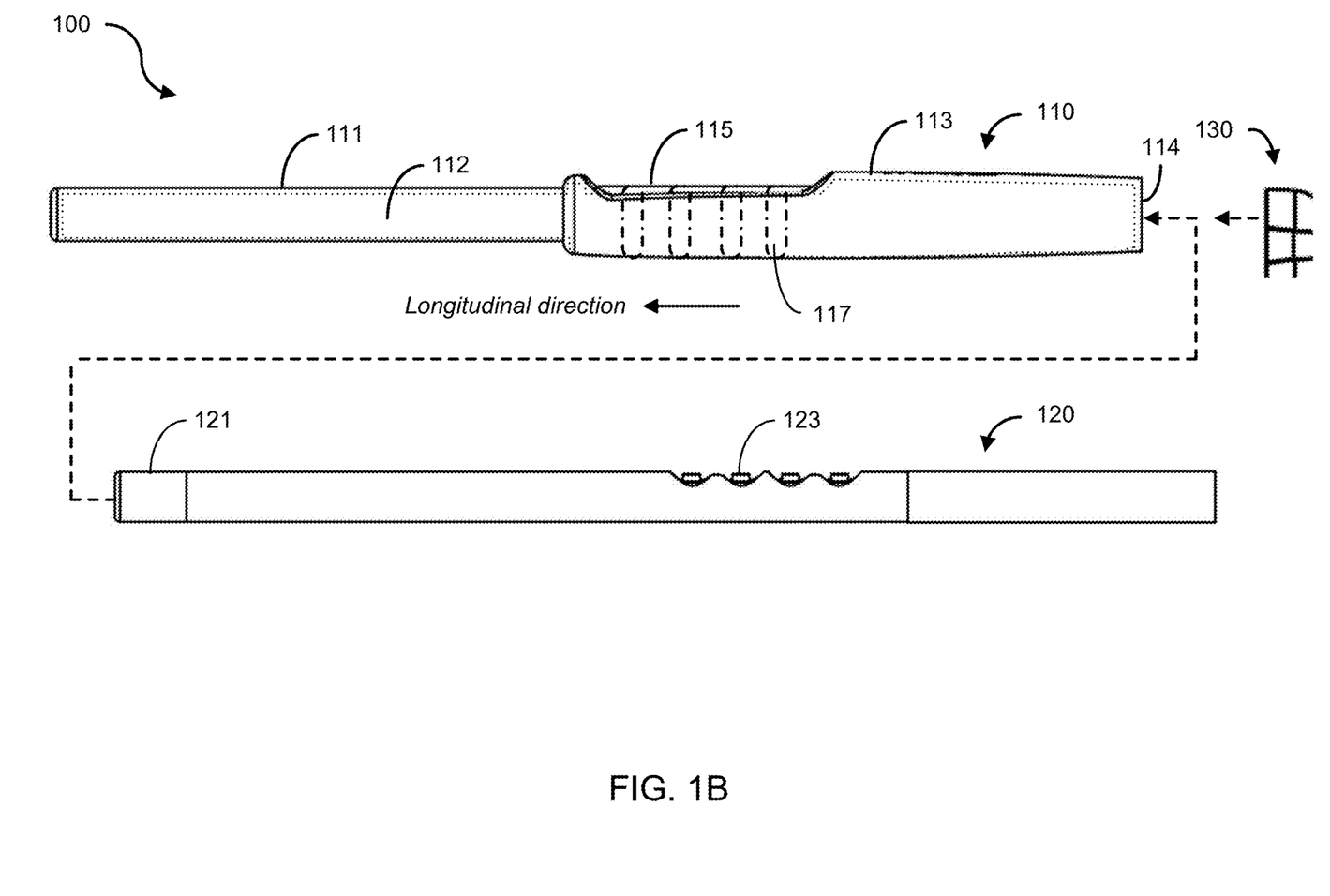

FIG. 1B shows an illustrative diagram of an example embodiment of the surgical device 100, in which the exterior casing unit 111 includes one or more rings 117 that span along, at least a portion of, the surface of the interior cavity 112 in the region of the flexible membrane 115 to radially align with the set of operable controls of the surgical probe 120 to allow for actuation of the apparatus' controls by tactile interaction of a user's appendage (e.g., finger(s)) with the set of operable controls 123, via the one or more rings 117. For example, the one or more rings 117 can allow the user to insert the surgical apparatus 120 within the exterior shell casing 110 without having to precisely align the set of operable controls 123 at a certain point or region along the circumference of the exoshell. In some examples, the rings 117 can be ribs of the material of the exterior shell casing 110 that protrude inward and wrap around at least a portion of the interior cavity 112. In some examples the rings 117 may also protrude outward from the exterior of the exoshell. Whereas, in some examples, the one or more rings 117 can include capacitive contacts that are configured to facilitate a touch interaction with corresponding capacitive contacts of the set of operable controls 123.

Figure 1C:
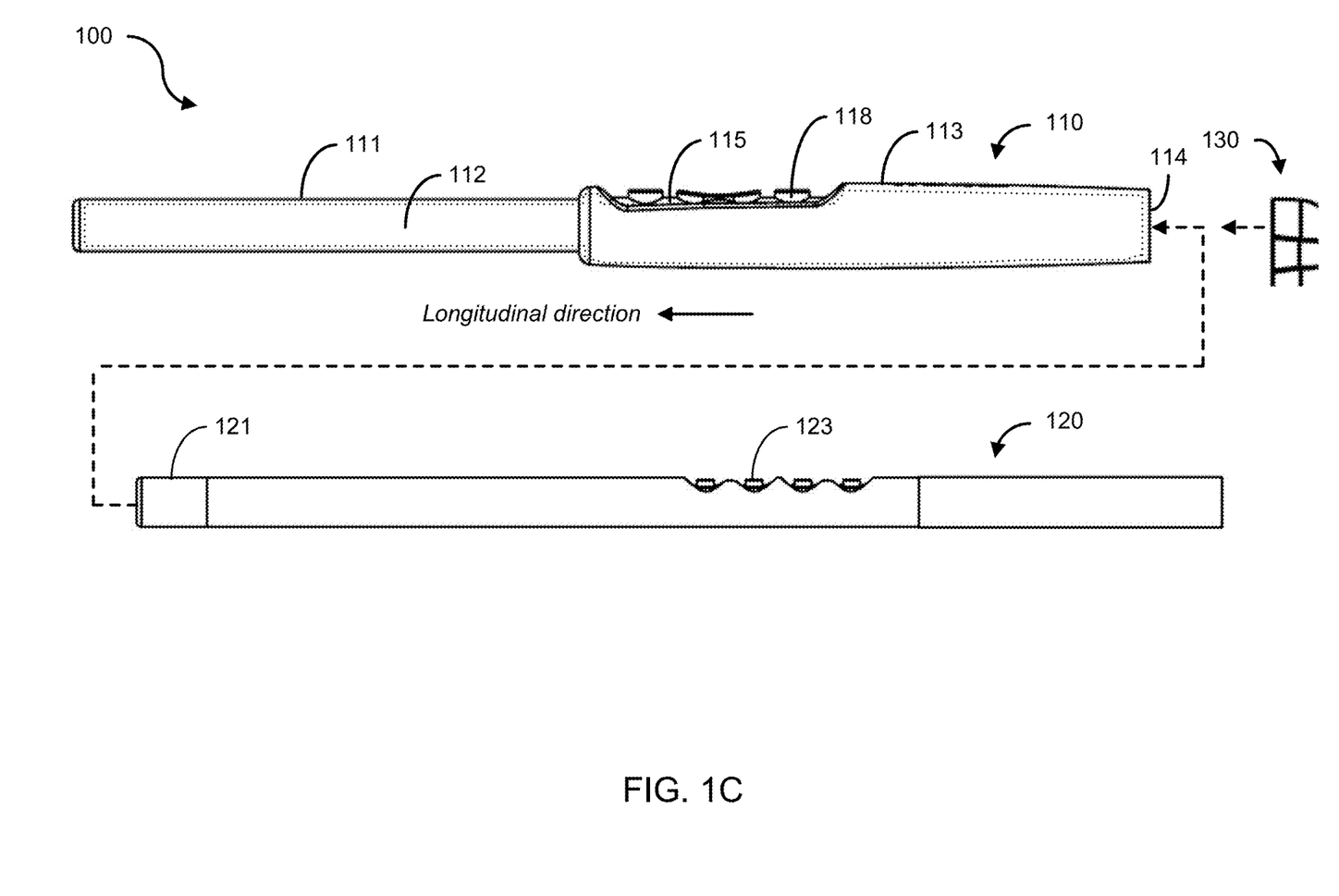

FIG. 1C shows an illustrative diagram of an example embodiment of the surgical device 100, in which the flexible membrane 115 includes one or more buttons 118 that interface with the set of operable controls of the surgical probe 120 to allow for actuation of the apparatus' controls by tactile interaction of a user's appendage (e.g., finger(s)) with the set of operable controls 123, via the buttons 118.

In some embodiments, the exterior shell casing 110 can include a guide fixture configured on the surface of the interior cavity 111 located in the second region 113 proximate to the opening 114. In some examples, the guide fixture can include a funnel shape to facilitate aseptic insertion of the surgical apparatus 120 into the interior cavity 111 through opening 114. In some examples, the guide fixture is reversibly attachable to the surface of the interior cavity 111 to allow the guide fixture to be positioned within the interior cavity proximate the opening and removable from the interior cavity 111 prior to closing the exterior shell casing with the end cap 130.

In some embodiments, one or both of the exterior shell casing 110 and the surgical apparatus 120 can include alignment markers to indicate alignment of the surgical probe within the exterior shell casing. For example, the alignment markers indicate a proper orientation of the surgical probe within the exterior shell casing. In some implementations, the alignment markers can be placed on an interior surface of the exterior shell casing 110 in the second region 113, whereas in some implementations, the alignment markers can be placed on an exterior surface of the exterior shell casing 110 in the second region 113.

Figure 2:
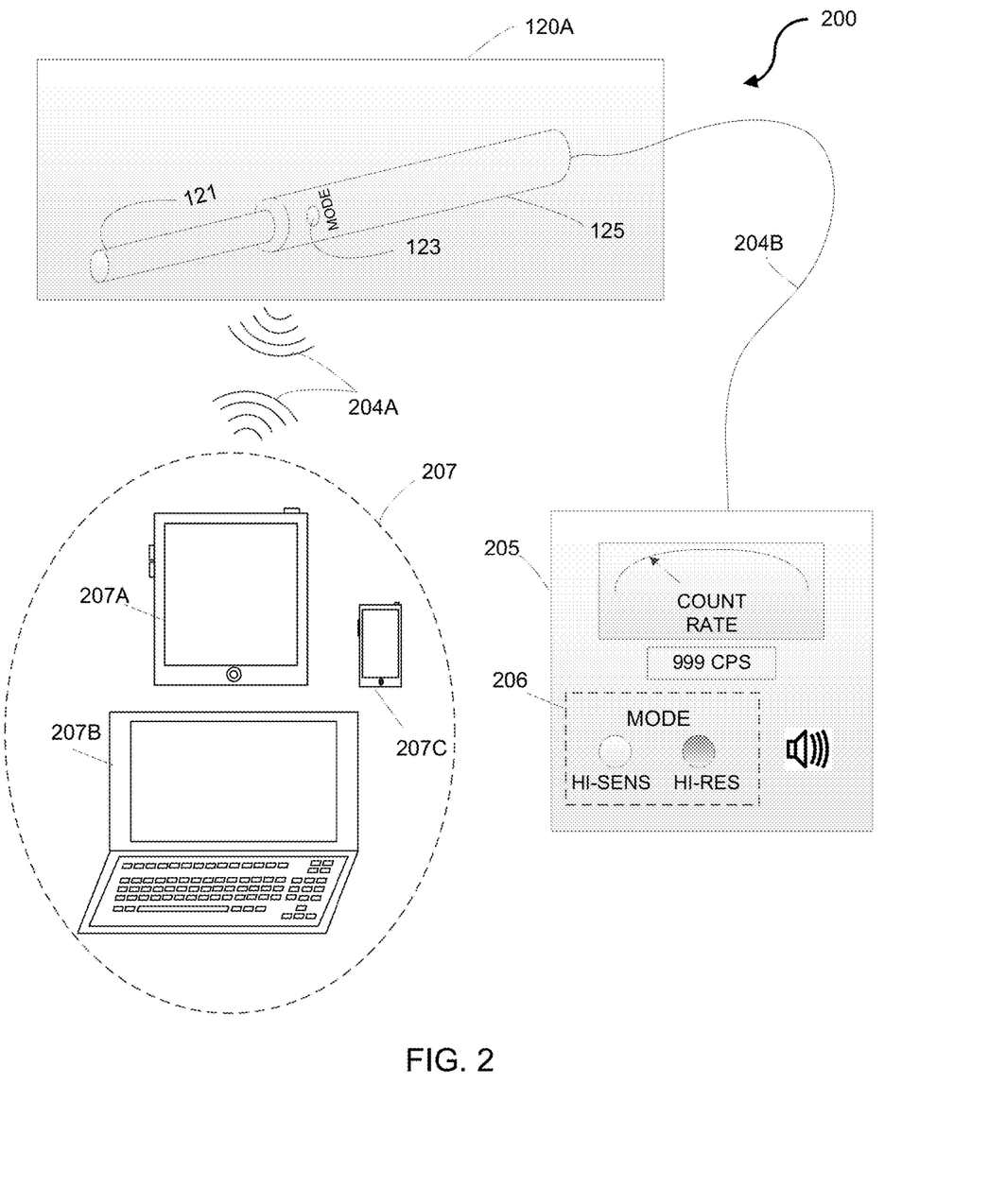
FIG. 2 shows a diagram of an example nuclear-uptake probe system that incorporates a separate user feedback device in communication with a handheld probe device.

FIG. 2 shows a diagram of an example nuclear-uptake probe system 200, including a processing system, such as an external probe system control unit 205, for processing the counts data received from a nuclear-uptake probe device 120A (i.e., a handheld probe). The nuclear-uptake probe device 120 includes the probe detector 121, the set of operable controls 123, and a proximal region 125 for the user to hold the device 120A and operate the controls 123. In some embodiments, the hand-held nuclear-uptake probe device 120A includes an internal data processing unit, comprising a processor and a memory, in communication with the probe detector 121 and the set of operable controls 123 to process data. For example, the data processing unit can process the detected signals obtained at the probe detector 121 and the actuation of controls of the set of operable controls 123.

In some embodiments, the set of operable controls 123 of the hand-held nuclear-uptake probe device 120A includes a mode controller, such as mode switch and/or display, which can be located on and integrated into the device 120A, giving the user direct access to a mechanism for changing or switching between multiple energy acceptance windows from a sterile surgical field 103. For example, the user can switch between multiple nuclear-uptake modes by simply interacting with the mode switch without interruption and without having to move or look away from the tissue area being surveyed. As such, the user is able to identify the location of the concentration of radionuclide emitting signals from deep structures or regions within the surveyed area.

The nuclear-uptake probe system 200 includes a communication medium, such as a wireless communication medium 204A and/or a wired communication medium 204 (e.g., depicted by a cable), which can be used to transmit electronic signals between the handheld probe and the external probe system control unit 205. In some implementations, the wireless connection can include an RF wireless link to provide more freedom in moving the nuclear-uptake probe device 120A around during surgery. The external probe system control unit 205, may include an indicator 206, displaying the current energy acceptance window mode selection. The indicator 206, can display the selected energy acceptance window using various graphical presentations including physical indicator lights integrated into the external probe system control unit 205, virtual indicator lights displayed on a display device (not shown), names of the selected nuclear-uptake modes displayed on a display device, or other similar visual indications.

In some implementations, the indicator 206 can include an audio indicator in addition to, or instead of, a visual indicator. Examples of audio indicators include various audible sounds that identify the selected nuclear-uptake mode to the surgeon without requiring the surgeon to look at a display panel or indicator on the external probe system control unit 205. The various audible sounds can include different tones to represent different modes or the actual names of the different modes. In addition, other similar visual and audio indicators can be implemented.

In some embodiments, the indicator 206 (e.g., visual, audio, and/or tactile indicators) can be integrated into the hand-held nuclear-uptake probe device 120A, e.g., to provide feedback that identifies the selected nuclear-uptake mode without distracting or interrupting the user. Thus, the user can obtain feedback on the selected nuclear-uptake mode without interruption and without moving away or looking away from the survey area.

Figure 3:
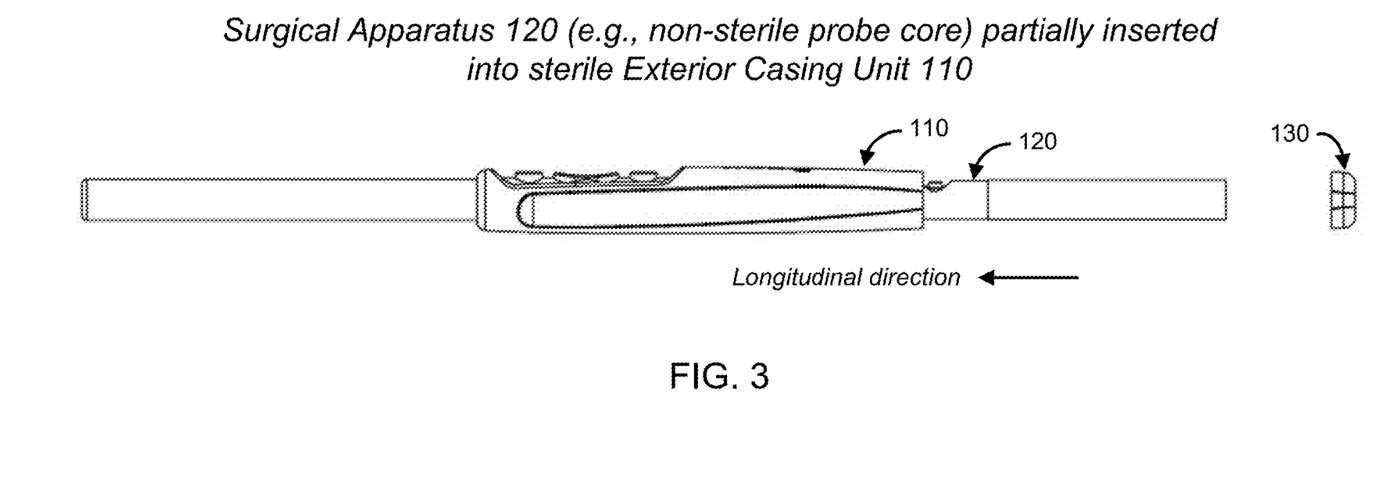
FIG. 3 shows a diagram illustrating insertion of an example surgical probe in an open end of an example exterior shell casing structure.

FIG. 3 shows a diagram illustrating insertion of an example embodiment of the surgical apparatus 120 (e.g., non-sterile, durable probe core 120A) into the opening 114 of the exterior shell casing 110 (e.g., sterile, disposable exoshell). The surgical apparatus 120 is inserted in an aseptic manner along a longitudinal direction such that the operable controls of the apparatus align with the region of the exterior shell casing 110 where the flexible membrane 115 is disposed. In some example implementations where the exterior shell casing 110 includes a flexible membrane sheath or flexible buttons, the surgical apparatus 120 should be inserted such that the operable controls are along the radial direction to align with the flexible membrane sheath or the flexible buttons. In some example implementations where the exterior shell casing 110 includes rings that span along the circumference, at least partially, of the interior in the region of the flexible membrane 115, the surgical apparatus 120 can be inserted such that the operable controls align with a portion of the rings.

Figure 4:
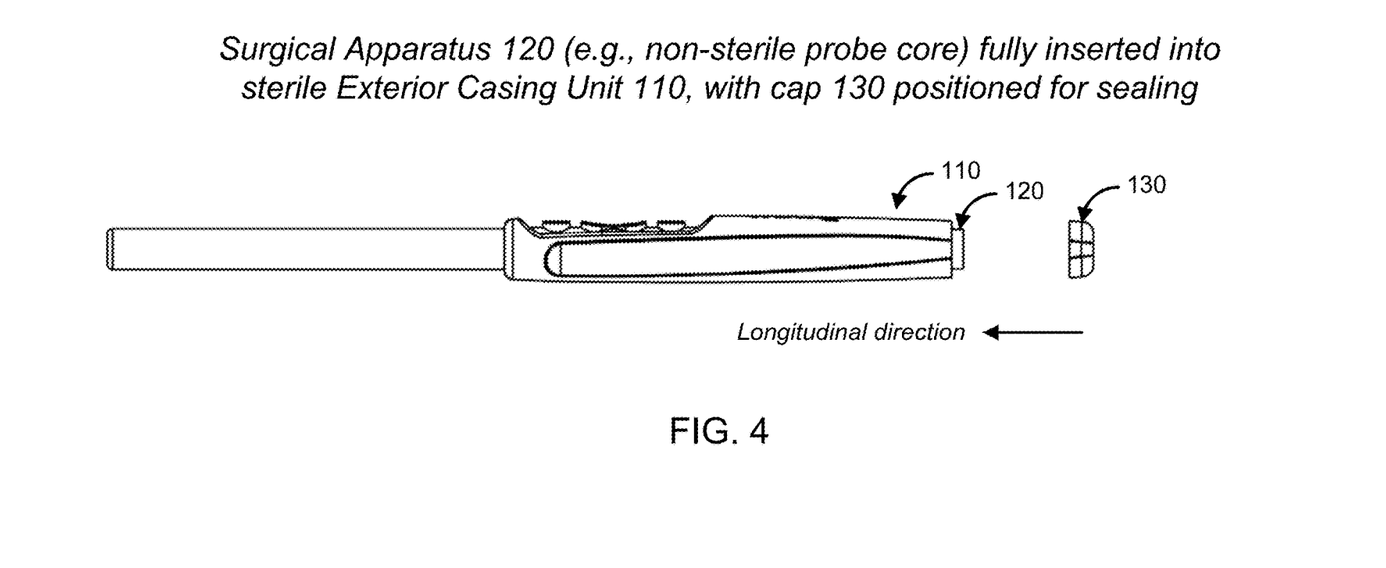
FIG. 4 shows a diagram illustrating closure of an end cap on the example exterior shell casing structure in FIG. 3.

FIG. 4 shows a diagram illustrating closure of the open end of the exterior shell casing 110 and end cap 130 (e.g., sterile, disposable exoshell) with the sterile end cap 130. The end cap 130 can seal the surgical apparatus 120 in the exoshell, thereby making the overall surgical device a sterile device regardless of the sterility of the surgical apparatus prior to insertion.

Figure 5:
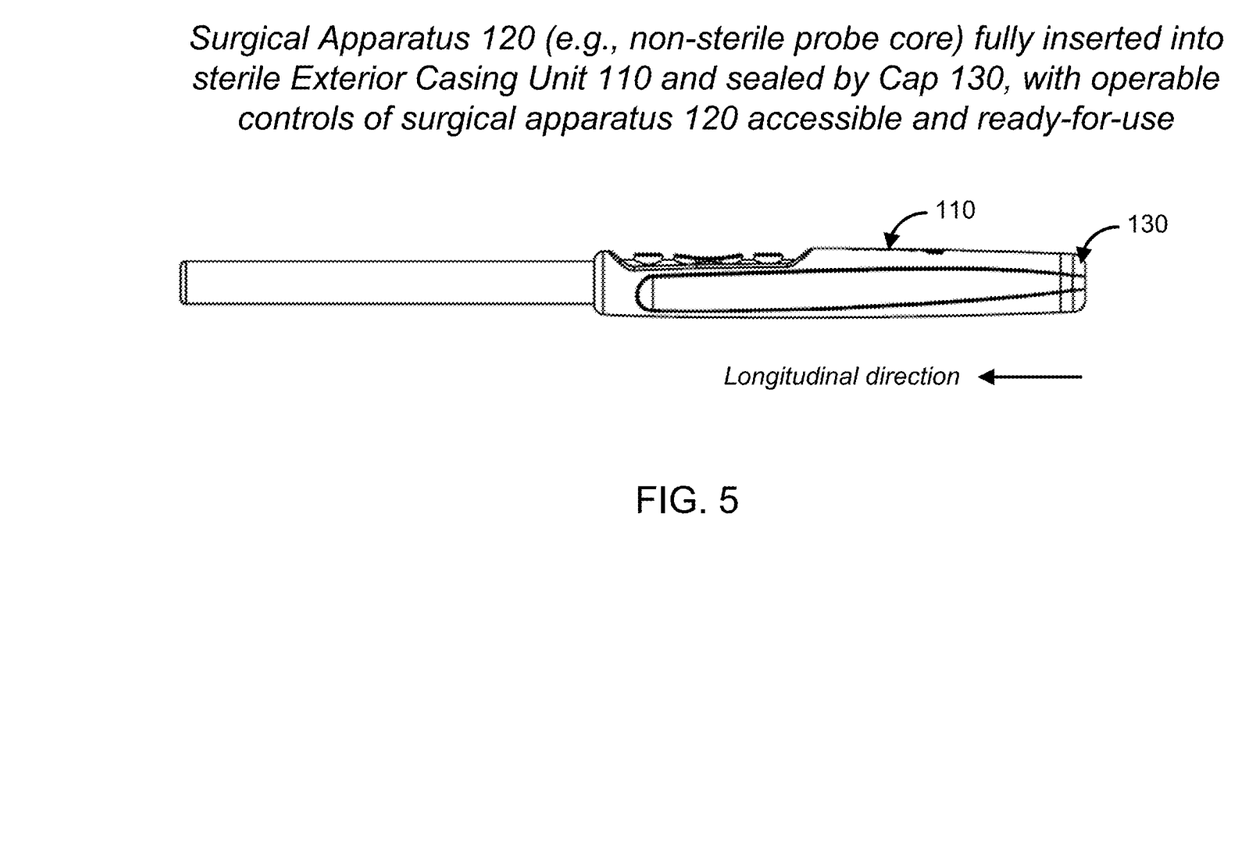
FIG. 5 shows a diagram illustrating the example surgical device having the example surgical probe fully enclosed by the example exterior shell casing structure.

FIG. 5 shows a diagram illustrating the surgical apparatus 120 (e.g., non-sterile probe core) fully enclosed by the exoshell with operable controls and ready for surgical use. The diagram also illustrates how a handle could be provided that surrounds the operable controls, e.g., assisting with the user's ability to stably hold the device and utilize the controls during medical procedures.

The example embodiments of the surgical device 100 and/or its constituents can include one or more of the following features.

In some examples, to facilitate aseptic insertion of the non-sterile probe core into the open end of the sterile exoshell, a sterile guide fixture can be included in the exterior shell casing 110, e.g., which can be a funnel in shape. The example guide fixture may be pre-positioned in the open end of the exterior shell casing 110, and could be removed prior to sealing the exterior shell casing 110 with the end cap 130 to form the exoshell.

The sterile, disposable exoshell can be made in various manners. For example, one method of manufacturing the exoshell includes by injection molding. As illustrated in the figures, the exoshell can be provided with a handle that surrounds the location of the operable controls. This handle could be made from pliable silicon rubber that can be over molded on the injection molded part. The silicon rubber handle could contain a region where the thickness of the rubber is thinned to create flexible membranes which, when positioned over the example probe core's operable controls for actuation, would constitute the operable controls on the sterile exoshell's surface.

In some embodiments, the end cap 130 can include an electrically conductive contact that electrically connects to an electrical interface on the surgical apparatus 120 (e.g., probe core) on the interior side of the contact and to a wire (e.g., a separate wire that can attach) on the outer side of the contact, which allows communication with an external processing device (e.g., external probe system control unit 205). Whereas, in some embodiments, the end cap 130 can include a hole and/or cut portion to allow for a wire pass out of the sterile, disposable exoshell for examples of the surgical apparatus 120 that utilize wired communication with an external processing device (e.g., external probe system control unit 205). Notably, the examples shown in the figures facilitate wireless communication between the surgical apparatus 120 encased in the exoshell with the external controller using wireless communication.

In some embodiments, the end cap 130 and the external shell casing 110 can be one integrated piece, e.g., where the closure cap that is attached to the shell casing.

In some embodiments, for example, to facilitate alignment of the probe cores operable controls to those on the surface of the exoshell, alignment marks and/or structures could be positioned on both.

Notably, re-use of sterile, disposable surgical devices is sometimes attempted in an effort to reduce the cost of use per procedure. However, this can often be a false economy, as failure to re-establish the sterility of the device can lead to costly patient infections, let alone the dangers posed by such actions.

Based on the structure and materials of the exoshell, the exoshell may be implemented in applications where sterility of the exoshell is reestablished. For example, methods of re-establishing sterility of the exoshell can include draping the device with a pliable, sterile sheath or by removing the surgical apparatus 120 (e.g., probe core) and directly re-sterilizing the exoshell (e.g., autoclaving). As noted previously, draping can make it difficult for the surgeon to confidently use the device's controls as the overlying sheath reduces sensory perception of the location of the controls. Also noted is that pliable sheaths are not free from perforations.

In some applications, for example, prior to the beginning of the surgery, it may be common practice for a surgeon to use a nuclear uptake probe to check that a patient has been injected with radioactive material. Rarely from the time of this check to the end of the surgical procedure will more than 4 hours of time elapse. Additionally, very rarely will a nuclear uptake probe procedures require more than 100 minutes of probe use.

As such, to defeat the potential for repeated use of the sterile exoshell, the surgical device 100 can be configured with electronic unit for determining the time of first use of the exoshell, and then prevent the same exoshell from being re-used after a specified period of time from its first use. Additionally or alternatively, for example, the electronic unit could be used to limit the duration of time of use of the exoshell to a specified period of time. Additional or other measures to defeat reuse of the exoshell can include making it necessary to break the exoshell to remove the probe core after use.

Other Example Applications

The sterile exoshell could also be provided with a light (e.g., LED, fiber optic, or other illuminator) on the distal end which, when actuated by a control on the surface of the exoshell, could be used to illuminate the interior of the incision into which the probe is inserted.

Another application of the sterile exoshell would be to provide electrical insulation of the probe system. This could help prevent the interference of the probe's operation caused by accidental contact of the probe with an operating electrosurgical tool.

Another application of the sterile exoshell would be to incorporate into the distal end of the exoshell an antenna for transmitting/receiving an RF signal used to stimulate an RFID tag placed in a patient for the purpose of marking the location of a tumor.

Another application of the sterile exoshell would be on a nuclear uptake probe that does not have controls.

Examples

In some embodiments in accordance with the present technology, a surgical device includes a sterile exoshell having (i) a distal end for insertion into an incision, (ii) a proximal end with a handle having operable controls on its surface, and (iii) an opening in the exoshell allowing access to the core of the exoshell; a gamma probe having operable controls (e.g., a mechanical switch, a capacitive contact, a Hall sensor, a touch display, or other mechanism) and that is configured to be inserted into the core of the exoshell, and a means whereby when inserted into the core of the exoshell the operable controls of the gamma probe are aligned with the operable controls on the surface of the exoshell such that the actuation of the controls on the surface of the exoshell affect actuation of the gamma probe controls; and a sterile cap or lid that covers the opening of the sterile exoshell thereby completely enclosing the inserted gamma probe within a sterile surface.

In some embodiments in accordance with the present technology (example 1), a surgical device includes a surgical probe, including a probe detector located in a distal region of the surgical probe, a set of operable controls located in a proximal region of the surgical probe to allow a user to affect one or more parameters of the probe detector, and a data processing unit to process data associated with the probe detector and the set of operable controls; an exterior shell casing including a first region and a second region, the exterior shell casing structured to include an opening at one end in the second region and an interior cavity of a size and shape to fit the surgical probe within the exterior shell casing that positions the probe detector in the first region and positions the set of operable controls in the second region, which the first region of the exterior shell casing is configured to be inserted into an incision of a body and the second region is configured to provide access to the set of operable controls of the surgical probe; and an end cap attachable to the exterior shell casing to close the opening.

Example 2 includes the surgical device of example 1 or any of the subsequent examples, of which the exterior shell casing and the end cap are sterile on at least an outer surface and able to preserve sterility of the surgical device including when the probe device is non-sterile.

Example 3 includes the surgical device of any of the preceding or subsequent examples, of which the exterior shell casing includes a flexible membrane that aligns with the set of operable controls of the surgical probe to allow for actuation of the set of operable controls by tactile interaction of a user's hand with the operable controls through the flexible membrane.

Example 4 includes the surgical device of any of the preceding or subsequent examples, of which the exterior shell casing includes a guide fixture having a funnel shape to facilitate aseptic insertion of the surgical probe into the interior cavity through opening.

Example 5 includes the surgical device of example 4, of which the guide fixture is reversibly attachable to the interior cavity to allow the guide fixture to be positioned within the interior cavity proximate the opening and removable from the interior cavity prior to closing the exterior shell casing with the end cap.

Example 6 includes the surgical device of any of the preceding or subsequent examples, of which the second region of the exterior shell casing includes a handle portion surrounding the location of the set of operable controls of the surgical probe.

Example 7 includes the surgical device of example 6, of which the handle portion includes pliable silicon rubber.

Example 8 includes the surgical device of any of the preceding or subsequent examples, of which the exterior shell casing and the surgical probe each include alignment markers to indicate alignment of the surgical probe within the exterior shell casing.

Example 9 includes the surgical device of example 8, of which the alignment markers indicate a proper orientation of the surgical probe within the exterior shell casing.

Example 10 includes the surgical device of any of the preceding or subsequent examples, of which the exterior shell casing includes a flexible portion including one or more rings that span along at least a portion of a respective radial axis in the flexible portion to radially align with the set of operable controls of the surgical probe to allow for actuation of the set of operable controls by tactile interaction of a user's hand with the operable controls.

Example 11 includes the surgical device of any of the preceding or subsequent examples, further including a timer module, of the data processing unit, to measure a duration of time of use of the surgical device in a surgical procedure.

Example 12 includes the surgical device of example 11, of which the data processing unit is operable to detect use of the surgical device based on operation of one or more of the operable controls.

Example 13 includes the surgical device of example 11, of which the data processing unit is operable to detect use of the surgical device based on operation of the probe detector.

Example 14 includes the surgical device of any of the preceding or subsequent examples, further including an optical, auditory or haptic indicator to produce a signal associated with a first time use of the surgical device.

Example 15 includes the surgical device of any of the preceding or subsequent examples, of which the surgical probe includes a display disposed in the proximal region to display at least one of data associated with the probe detector or a setting associated with the operable controls, and of which the exterior shell casing includes a thin membrane sheath that is optically translucent or transparent to allow viewing of the display.

Example 16 includes the surgical device of any of the preceding or subsequent examples, of which the exterior shell casing includes a locking mechanism to cause a user to break the exterior shell casing and/or the end cap to remove the surgical probe after use, thereby preventing reuse of the exterior shell casing and/or the end cap of the surgical device.

Example 17 includes the surgical device of any of the preceding or subsequent examples, further including a light disposed on the second region of the exterior shell casing and operable, when actuated by a control of the set of operable controls, to illuminate the interior of the incision into which the surgical device is inserted.

Example 18 includes the surgical device of any of the preceding or subsequent examples, further including an antenna operable to transmit and/or receive an RF signal for stimulating an RFID tag placed in a patient capable of marking a location of a target tissue.

Example 19 includes the surgical device of any of the preceding or subsequent examples, of which the exterior shell casing is operable to provide electrical insulation of the surgical probe.

Example 20 includes the surgical device of any of the preceding or subsequent examples, of which the exterior shell casing includes a biocompatible material including a polycarbonate or polysulfone material.

Example 21 includes the surgical device of any of the preceding or subsequent examples, of which the exterior shell casing is configured to provide direct sensory contact of a user to the set of operable controls of the surgical probe.

Example 22 includes the surgical device of any of the preceding examples, of which the surgical probe includes a gamma probe including a collimator and a radiation sensor to detect a radionuclide.

In some embodiments in accordance with the present technology (example 23), a sterile exoshell for a handheld surgical apparatus includes an exterior shell casing including a first region and a second region, the exterior shell casing structured to include an opening at one end in the second region and an interior cavity of a size and shape to fit a surgical apparatus within the exterior shell casing that positions a first component in the first region and positions a set of operable controls that affect one or more parameters of the first component in the second region, the exterior shell casing including a control interface structure located in the second region to allow utilization of the set of operable controls through the exterior shell casing, the first region of the exterior shell casing is configured to be inserted into an incision of a body and the second region is configured to provide access to the set of operable controls of the surgical probe; and an end cap attachable to the exterior shell casing to close the opening.

Example 24 includes the exoshell of any of example 23 or subsequent examples, which the surgical apparatus includes a surgical probe, which the first component includes a probe detector located in a distal region of the surgical probe, and the set of operable controls is located in a proximal region of the surgical probe to allow a user to affect the one or more parameters of the probe detector, which the surgical probe includes a data processing unit to process data associated with the probe detector and the set of operable controls.

Example 25 includes the exoshell of any of the preceding or subsequent examples, of which the exterior shell casing and the end cap are sterile on at least an outer surface and able to preserve sterility of the surgical apparatus including when the surgical apparatus is non-sterile.

Example 26 includes the exoshell of any of the preceding or subsequent examples, of which the control interface structure includes a flexible membrane that aligns with the set of operable controls of the surgical apparatus to allow for actuation of the set of operable controls by tactile interaction of a user's hand with the operable controls through the flexible membrane.

Example 27 includes the exoshell of any of the preceding or subsequent examples, of which the exterior shell casing includes a guide fixture having a funnel shape to facilitate aseptic insertion of the surgical apparatus into the interior cavity through opening.

Example 28 includes the exoshell of example 27, of which the guide fixture is reversibly attachable to the interior cavity to allow the guide fixture to be positioned within the interior cavity proximate the opening and removable from the interior cavity prior to closing the exterior shell casing with the end cap.

Example 29 includes the exoshell of any of the preceding or subsequent examples, of which the second region of the exterior shell casing includes a handle portion surrounding the location of the set of operable controls of the surgical apparatus.

Example 30 includes the exoshell of any of the preceding or subsequent examples, of which the exterior shell casing includes a biocompatible material including a polycarbonate or polysulfone material.

Example 31 includes the exoshell of any of the preceding or subsequent examples, of which the exterior shell casing includes an alignment marker to indicate alignment of the surgical apparatus within the exterior shell casing.

Example 32 includes the exoshell of any of the preceding or subsequent examples, of which the exterior shell casing includes a locking mechanism to cause a user to break the exterior shell casing and/or the end cap to remove the surgical apparatus after use, thereby preventing reuse of the exterior shell casing and/or the end cap.

Example 33 includes the exoshell of any of the preceding or subsequent examples, further including a light disposed on the second region of the exterior shell casing and operable, when actuated by a control of the set of operable controls, to illuminate the interior of the incision into which the surgical device is inserted.

Example 34 includes the exoshell of any of the preceding or subsequent examples, of which the exterior shell casing is operable to provide electrical insulation of the surgical apparatus.

Example 35 includes the exoshell of any of the preceding or subsequent examples, of which the exterior shell casing is configured to provide direct sensory contact of a user to the set of operable controls of the surgical apparatus.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A surgical device, comprising:
    a surgical probe, including a probe detector located in a distal region of the surgical probe, a set of operable controls located in a proximal region of the surgical probe to allow a user to affect one or more parameters of the probe detector, and a data processing unit to process data associated with the probe detector and the set of operable controls;
    an exterior shell casing including a first region and a second region, the exterior shell casing structured to include an opening at one end in the second region and an interior cavity of a size and shape to fit the surgical probe within the exterior shell casing that positions the probe detector in the first region and positions the set of operable controls in the second region, the exterior shell casing including a plurality of projections that protrude inward within the interior cavity and a control interface structure located in the second region and aligned with the plurality of projections, wherein the plurality of projections are spaced apart rings that extend circumferentially along a surface of the interior cavity, wherein when the surgical probe is disposed within the exterior shell casing, the plurality of projections are radially aligned with the set of operable controls so as to allow operation thereof through the exterior shell casing, wherein the first region of the exterior shell casing is configured to be inserted into an incision of a body and the second region is configured to provide access to the set of operable controls of the surgical probe; and
    an end cap attachable to the exterior shell casing to close the opening.

2. The surgical device of claim 1, wherein the exterior shell casing and the end cap are sterile on at least an outer surface and able to preserve sterility of the surgical device including when the surgical probe is non-sterile.

3. The surgical device of claim 1, wherein the control interface structure includes a flexible membrane that aligns with the set of operable controls of the surgical probe to allow for actuation of the set of operable controls by tactile interaction of a user's hand with the operable controls through the flexible membrane.

4. The surgical device of claim 1, wherein the exterior shell casing includes a guide fixture having a funnel shape to facilitate aseptic insertion of the surgical probe into the interior cavity through the opening.

5. The surgical device of claim 4, wherein the guide fixture is reversibly attachable to the interior cavity to allow the guide fixture to be positioned within the interior cavity proximate the opening and removable from the interior cavity prior to closing the exterior shell casing with the end cap.

6. The surgical device of claim 1, wherein the second region of the exterior shell casing includes a handle portion surrounding the location of the set of operable controls of the surgical probe.

7. The surgical device of claim 1, wherein the exterior shell casing includes a biocompatible material including a polycarbonate or polysulfone material.

8. The surgical device of claim 1, wherein one or both of the exterior shell casing and the surgical probe include an alignment marker to indicate alignment of the surgical probe within the exterior shell casing.

9. The surgical device of claim 8, wherein the alignment marker indicates a proper orientation of the surgical probe within the exterior shell casing.

10. The surgical device of claim 1, further comprising:
    a timer module, of the data processing unit, to measure a duration of time of use of the surgical device in a surgical procedure.

11. The surgical device of claim 10, wherein the data processing unit is operable to detect use of the surgical device based on operation of one or more of the operable controls.

12. The surgical device of claim 10, wherein the data processing unit is operable to detect use of the surgical device based on operation of the probe detector.

13. The surgical device of claim 1, further comprising:
    an optical, auditory or haptic indicator to produce a signal associated with a first time use of the surgical device.

14. The surgical device of claim 1, wherein the surgical probe includes a display disposed in the proximal region to display at least one of data associated with the probe detector or a setting associated with the operable controls, and wherein the exterior shell casing includes a thin membrane sheath that is optically translucent or transparent to allow viewing of the display.

15. The surgical device of claim 1, wherein the exterior shell casing includes a locking mechanism to cause a user to break the exterior shell casing and/or the end cap to remove the surgical probe after use, thereby preventing reuse of the exterior shell casing and/or the end cap of the surgical device.

16. The surgical device of claim 1, further comprising:
    a light disposed on the second region of the exterior shell casing and operable, when actuated by a control of the set of operable controls, to illuminate the interior of the incision into which the surgical device is inserted.

17. The surgical device of claim 1, further comprising:
    an antenna operable to transmit and/or receive an RF signal for stimulating an RFID tag placed in a patient capable of marking a location of a target tissue.

18. The surgical device of claim 1, wherein the exterior shell casing is operable to provide electrical insulation of the surgical probe.

19. The surgical device of claim 1, wherein the exterior shell casing is configured to provide direct sensory contact of a user to the set of operable controls of the surgical probe.

20. The surgical device of claim 1, wherein the surgical probe includes a gamma probe including a collimator and a radiation sensor to detect a radionuclide.

21. The surgical device of claim 1, wherein each of the spaced apart rings correspond to an operable control of the set of operable controls.

\* \* \* \* \*